United States Patent [19]

Ritter

[11] Patent Number: 5,153,962
[45] Date of Patent: Oct. 13, 1992

[54] FLUID POWERED BRUSH

[76] Inventor: Charles H. Ritter, 3219 Thomasville Rd.; #17A, Tallahassee, Fla. 32312

[21] Appl. No.: 611,042

[22] Filed: Nov. 9, 1990

[51] Int. Cl.⁵ .............................. A46B 13/06
[52] U.S. Cl. .......................... 15/28; 15/29; 4/606
[58] Field of Search .......... 15/24, 28, 29, 97.1; 128/56; 4/606

[56] References Cited

U.S. PATENT DOCUMENTS

| | | |
|---|---|---|
| 736,607 | 8/1903 | Lane ............................ 15/24 |
| 2,140,307 | 12/1938 | Belaschk et al. ............. 15/28 |
| 2,172,195 | 9/1939 | Elson ........................... 15/24 |
| 2,215,031 | 9/1940 | Elmore ......................... 15/28 |
| 3,869,746 | 3/1975 | Man-king ..................... 15/29 |
| 4,155,137 | 5/1979 | Kadlub .......................... 15/29 |
| 4,282,623 | 8/1981 | Gacuzana ..................... 15/29 |
| 4,793,331 | 12/1988 | Stewart ........................ 4/615 |
| 4,841,590 | 6/1989 | Terry et al. .................. 15/28 |

FOREIGN PATENT DOCUMENTS

| | | | |
|---|---|---|---|
| 0280833 | 9/1988 | European Pat. Off. ............ 15/29 |
| 478383 | 6/1929 | Fed. Rep. of Germany ........ 15/29 |

Primary Examiner—Edward L. Roberts
Attorney, Agent, or Firm—Shlesinger, Arkwright & Garvey

[57] ABSTRACT

The present invention generally relates to fluid powered brushes. A preferred embodiment is directed to a toothbrush powered by water enroute to a shower head. The toothbrush includes a handle and an operating head detachably connected thereto. A plurality of brush heads are positioned adjacent the operating head. A fluid driven impeller is disposed upstream of the outlet of the shower head. A flexible cable is connected at one end to the impeller and at the other end to the brush heads. The flexible cable rotates upon rotation of the impeller to drive the brush heads. A fluid powered toothbrush formed in accordance with the preferred embodiment of the present invention is adapted to efficiently drive multiple brush heads. Furthermore, no fluid need be drawn off the shower to power the toothbrush.

20 Claims, 3 Drawing Sheets

U.S. Patent  Oct. 13, 1992  Sheet 1 of 3  5,153,962
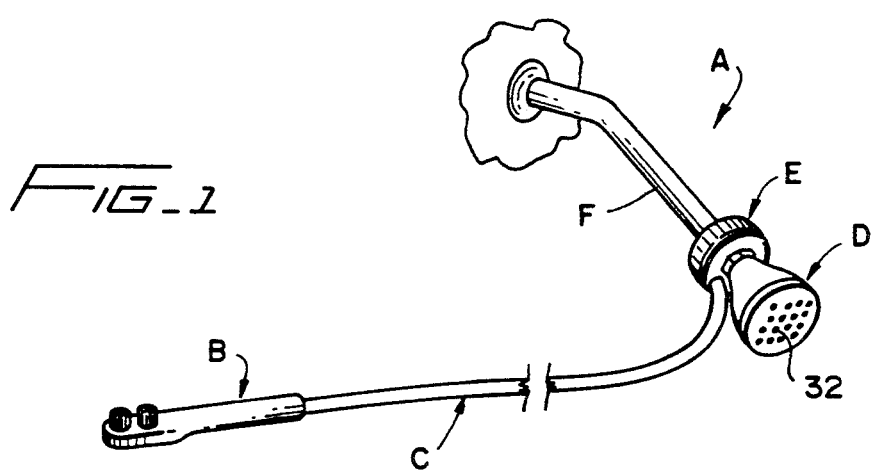
FIG_1
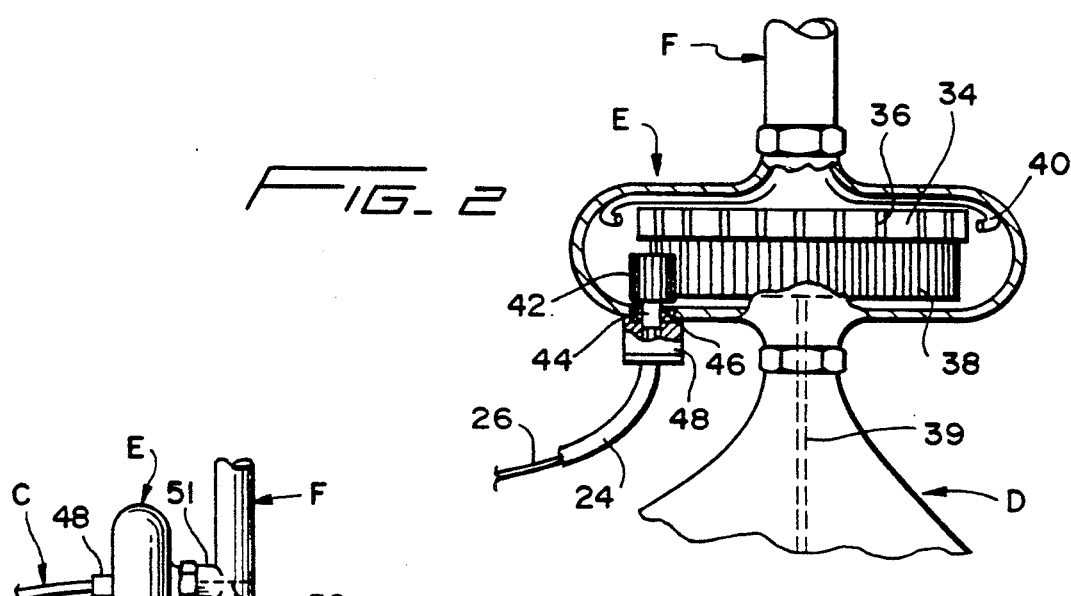
FIG_2
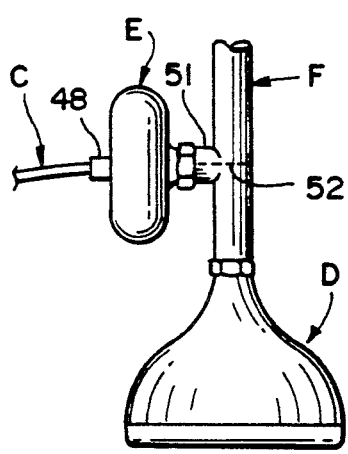
FIG_4
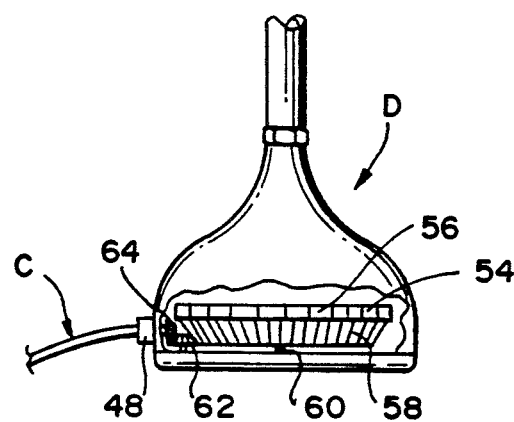
FIG_5

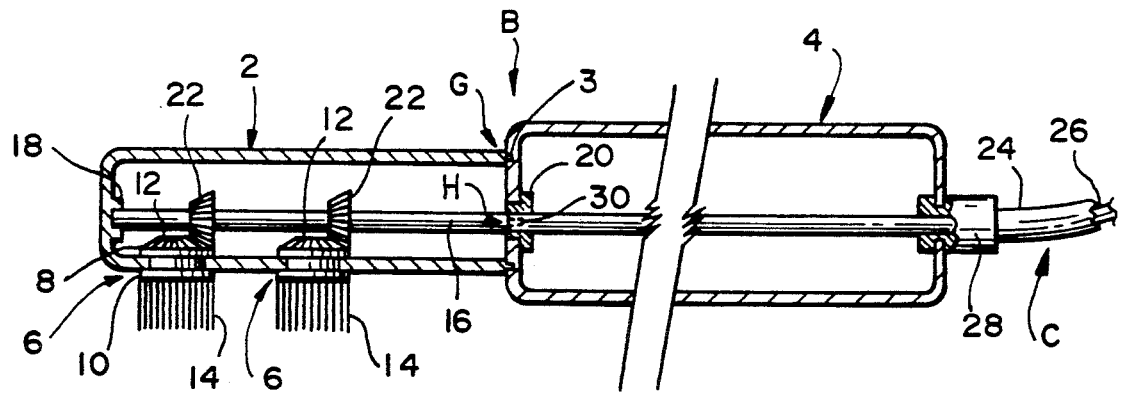
FIG_3
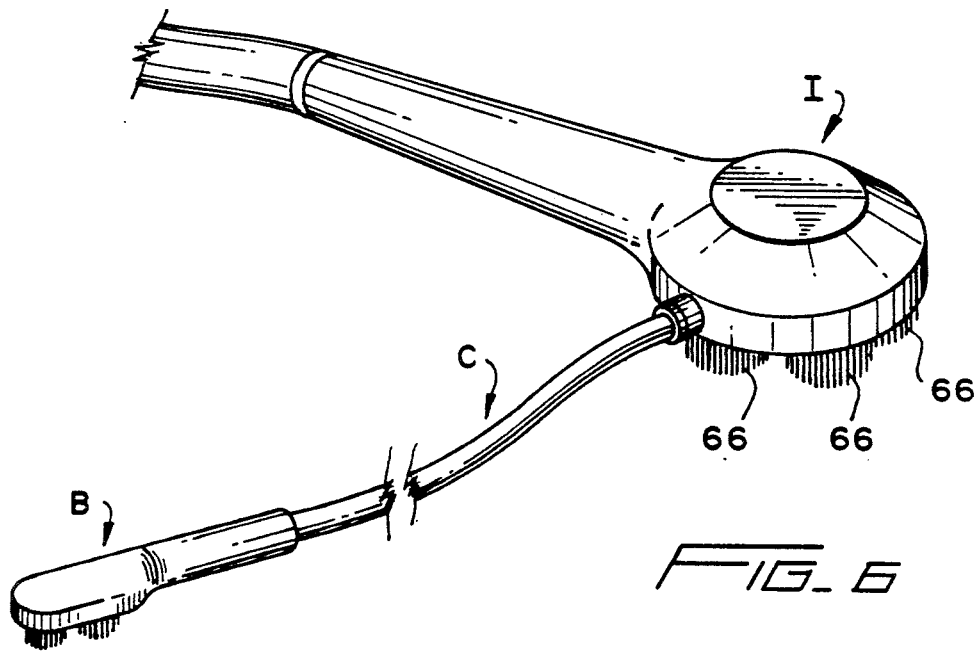
FIG_6
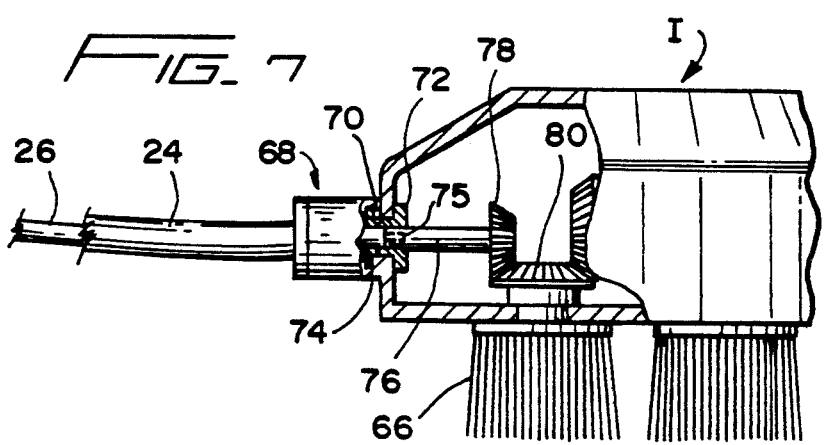
FIG_7

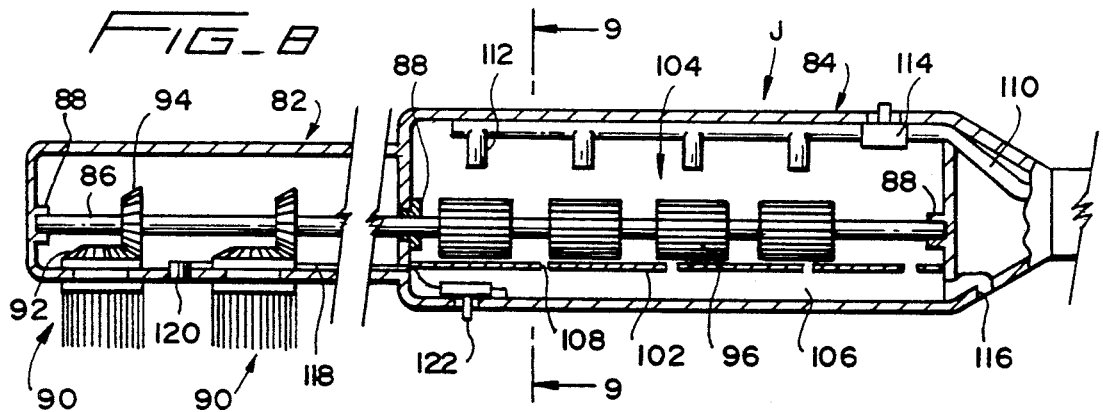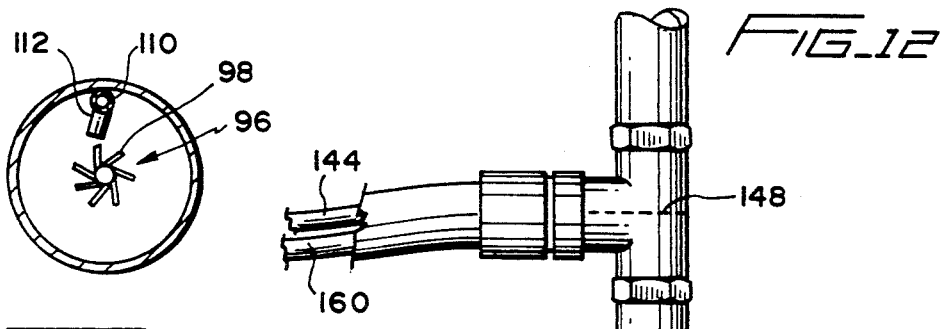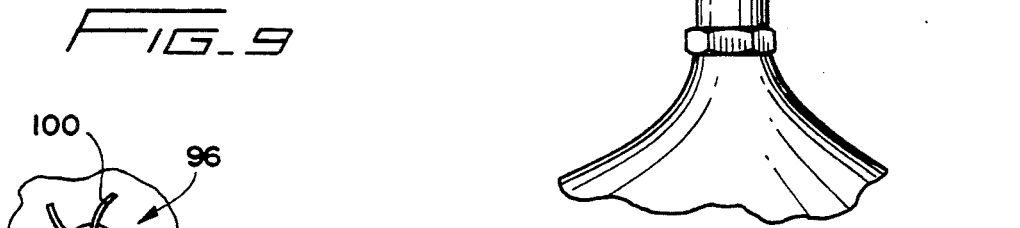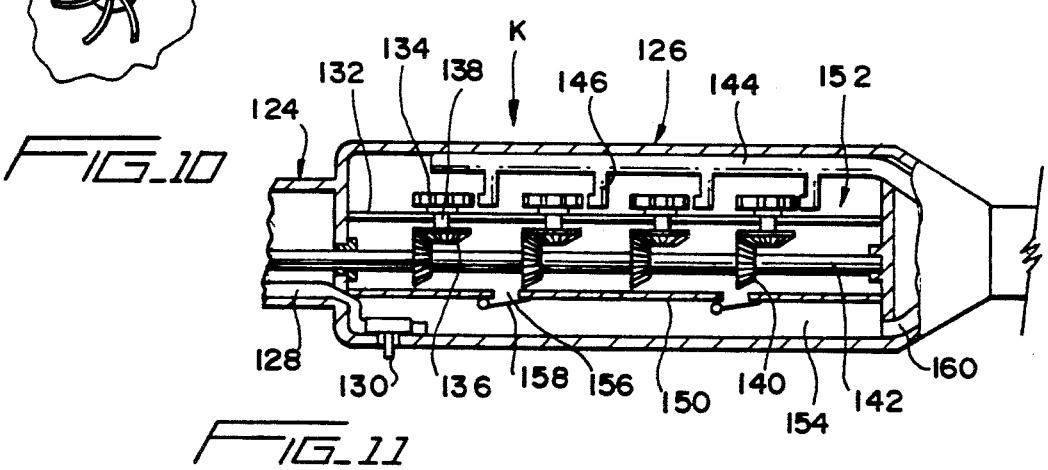

5,153,962

FLUID POWERED BRUSH

FIELD OF THE INVENTION

The present invention generally relates to fluid powered brushes. More specifically, a preferred embodiment of the present invention is directed to a toothbrush powered by water enroute to a shower.

BACKGROUND OF THE INVENTION

It has previously been known to power a brush implement by water enroute to a shower or a faucet. Implements of this general nature are illustrated in the following patent documents. U.S. Pat. Nos.: 3,869,746; 4,282,623; 4,793,331; and 4,841,590. However, these earlier proposed fluid powered brush implements have numerous disadvantages associated therewith, several of which are enumerated below.

For example, some known fluid powered brush implements draw off a significant portion or all of the fluid enroute to a shower or faucet to operate the same, thereby lessening or entirely eliminating the stream emitted by the shower or faucet. Moreover, systems of this type use a great deal more water in the operation thereof.

The drive system for several earlier proposed fluid powered brush implements are designed to accommodate only a single brush head. This is disadvantageous in that multiple brush heads normally result in a more thorough cleaning. Furthermore, multiple brush heads provide the user with a pleasing stimulation not found in brushes having a single brush head.

Finally, prior drive systems for fluid powered brushes having multiple brush heads are relatively inefficient. Drive systems of this type have an impeller fixed to each of the brush heads. The impellers are positioned on a common axis in the path of flow of the fluid. Thus, the force to drive the downstream impellers is substantially less than that for the upstream impeller resulting in slower rotating downstream brush heads.

OBJECTS AND SUMMARY OF THE INVENTION

An object of the present invention is to provide an improved fluid powered brush overcoming the disadvantages associated with the prior art.

Another object of the present invention is to provide a fluid powered brush for use with a fluid driven impeller which includes a body member having a horizontal axis and a brush means for scrubbing at least one portion of an individual's body. The brush means is positioned adjacent the body member. Connecting means is provided for drivingly connecting the brush means to a fluid driven impeller removed from the brush means along a horizontal axis of the body member. A fluid powered brush formed in the manner recited above is advantageous, for among other reasons, because the drive system thereof is more efficient than previously known fluid powered brushes.

Yet another object of the present invention is to provide a fluid powered brush system which includes a first brush having a body member and brush means for scrubbing at least one portion of an individual's body. The brush means is positioned adjacent the body member. The brush system further includes an impeller drive means adapted to be driven by a fluid for driving the brush means and connecting means for drivingly connecting the impeller drive means to the brush means. The impeller drive means is removed or offset from the brush means along a horizontal axis of the body member. By positioning the impeller drive means offset from the brush means along the horizontal axis of the body member, the fluid powered brush system can more efficiently drive multiple brush heads.

A further object of the present invention is to provide a fluid powered brush for use with a fluid driven impeller which includes a body member having a handle and an operating head and brush means for scrubbing at least one portion of an individual's body. The brush means is positioned adjacent the operating head. Connecting means is provided for drivingly connecting the brush means to a fluid driven impeller positioned removed from the body member. One advantage of a fluid powered brush formed in the manner recited above is that no fluid need be drawn from the water enroute to a shower or faucet to power the brush, since the connecting means connects the brush means to the fluid driven impeller at a location remote from the body member.

Yet still another object of the present invention is to provide a method of forming a fluid powered brush to be used with a fluid driven impeller which includes the steps of providing a body member having a handle and an operating head, providing brush means for scrubbing at least one portion of an individual's body, positioning the brush means adjacent the operating head and removed from a fluid driven impeller along a horizontal axis of the body member and providing connecting means for drivingly connecting the brush means to the fluid driven impeller. Because the brush means is positioned removed from the fluid driven impeller along a horizontal axis of the body member, the relative inefficiencies of previously known fluid powered brushes can be readily overcome.

Still another object of the present invention is to provide a method of driving a fluid powered brush system which includes the steps of providing a body member having a handle and an operating head, providing brush means for scrubbing at least one portion of an individual's body, providing at least one fluid driven impeller, positioning the fluid driven impeller remotely from the brush means along a horizontal axis of the body member and providing a fluid supply means for supplying a fluid to drive the fluid driven impeller. The above method for driving a fluid powered brush system is desirable in that it readily avoids substantial discrepancies in the drive force imparted on the various brush heads.

These objects and advantages as well as others will be readily apparent from the detailed description of the invention, the accompanying drawings and the attached claims.

In summary the present invention generally relates to fluid powered brushes. A preferred embodiment is directed to a toothbrush powered by water enroute to a shower head. The toothbrush includes a handle and an operating head detachably connected thereto. A plurality of brush heads are positioned adjacent the operating head. A fluid driven impeller is disposed upstream of the outlet of the shower head. A flexible cable is connected at one end to the impeller and at the other end to the brush heads. The flexible cable rotates upon rotation of the impeller to drive the brush heads. A fluid powered toothbrush formed in accordance with the preferred embodiment of the present invention is adapted to efficiently drive multiple brush heads. Furthermore, no fluid need be drawn off the shower to power the toothbrush.

DETAILED DESCRIPTION OF THE DRAWINGS

FIG. 1 is a fragmentary perspective view of a fluid powered brush system formed in accordance with a preferred embodiment of the present invention.

FIG. 2 is a plan view of the impeller housing with a portion thereof broken away.

FIG. 3 is a fragmentary cross-sectional view of the fluid powered brush.

FIG. 4 is a fragmentary plan view of a first alternative embodiment of the present invention.

FIG. 5 is a fragmentary plan view of a second alternative embodiment of the present invention.

FIG. 6 is a fragmentary perspective view of a third alternative embodiment of the present invention.

FIG. 7 is a fragmentary side view of the embodiment illustrated in FIG. 6 with a portion thereof broken away.

FIG. 8 is a fragmentary cross-sectional view of a fourth alternative embodiment of the present invention.

FIG. 9 is a sectional view taken along lines 9—9 of FIG. 8.

FIG. 10 is a side view of an alternative configuration for the vanes of the impellers.

FIG. 11 is a fragmentary cross-sectional view of a brush formed in accordance with a fifth alternative embodiment of the present invention.

FIG. 12 is a top plan view of the juncture at which the brush illustrated in FIG. 11 is connected to a shower head.

DETAILED DESCRIPTION OF THE INVENTION

The preferred embodiments of the present invention will be described hereinafter with reference made to the accompanying drawings.

FIGS. 1 THROUGH 3

Referring to FIG. 1, a fluid powered brush system A includes a toothbrush B, a flexible cord C, a shower head D, an impeller housing E, and a supply pipe F.

Referring to FIG. 3, the brush B includes an operating head 2 detachably connected to a handle 4 at G. Specifically, operating head 2 includes an annular member 3 which is inserted into a corresponding annular recess formed in handle 4. Preferably, the annular member 3 has a thickness which is equal to or slightly greater than the width of the recess in handle 4 to snugly secure the operating head 2 to handle 4. It will be readily appreciated that other conventional removable fastening arrangements may be used. A pair of brushes 6 are rotatably supported by operating head 2. Each of the brushes 6 include an upper surface 8 and a lower surface 10. A bevel gear 12 extends around the upper surface 8 of each of the brushes 6. A plurality of bristles 14 extend downwardly from the lower surface 10 of each of the brushes 6. Although two brushes 6 are shown, it will be readily appreciated that this number may be varied as desired.

An output shaft 16 extends substantially parallel to the horizontal axis of toothbrush B and is rotatably supported in operating head 2 by shoulders 18 and 20. A pair of bevel gears 22 are nonrotatably supported by shaft 16 directly above the bevel gears 12. The bevel gears 22 are disposed in meshing engagement with the corresponding bevel gears 12. Although the gear ratio for bevel gears 12 and 22 is depicted as being approximately 1 to 1, it will be readily appreciated that this ratio may be varied if it is desired to rotate one of brushes 6 at a faster rate.

The flexible cord C includes a protective sheath 24 and a flexible, rotatable cable 26. A support collar 28 is connected to handle 4 and rotatably supports cable 26 therein. The rotatable cable 26 extends substantially parallel to the horizontal axis of toothbrush B in handle 4 and is detachably connected to output shaft 16 at H. Output shaft 16 includes a pin 30 (shown in dotted lines) which is received in a corresponding hole in rotatable cable 26. The pin 30 preferably has a diameter equal to or slightly greater than the diameter of the hole formed in cable 26 to nonrotatably secure the output shaft 16 to cable 26. Other types of detachable fasteners may be used. For example, the pin 30 may be provided with a plurality of fins extending radially therefrom to be inserted into corresponding grooves extending outwardly from the outer periphery of the hole formed in cable 26. Such an arrangement would prevent any relative rotation between output shaft 16 and cable 26.

As seen in FIGS. 1 and 2, the impeller housing E is positioned upstream of the openings 32 of shower head D. An impeller 34, having a plurality of vanes 36 extending outwardly therefrom is nonrotatably secured to a gear 38. The impeller 34 and gear 38 are rotatably supported in impeller housing E by shaft 39. Shaft 39 is secured to shower head D at the end opposite impeller 34 and gear 38. Three supply conduits 40 (only two of which are shown) are equally spaced in impeller housing E and are secured to the inner surface thereof. The supply conduits 40 direct the fluid flowing through pipe F at the impeller 34 in order to rotate the same. A gear 42 is positioned in meshing engagement with gear 38 adjacent the periphery of housing E. Gear 42 includes a shaft 44 and is rotatably supported by bearings 46.

The flexible cord C includes a support collar 48 secured to the impeller housing E. The rotatable cable 26 passes through the support collar 48 and is nonrotatably fixed to shaft 44 of gear 42. Thus, cable 26 rotates upon rotation of impeller 34, which in turn causes brushes 6 to rotate. The gear ratio for gears 38 and 42 may be varied as desired.

This embodiment is a significant improvement over previously known fluid powered brush systems. Specifically, the drive force imparted on each of the brushes 6 is constant. Thus, the brushes 6 may be rotated at substantially the same speed if desired. Moreover, none of the fluid passing through pipe F is drawn off to drive toothbrush B. This aspect of the invention permits an individual to brush his or her teeth while taking a shower without in any way reducing the amount of fluid ultimately emitted by the shower head E. Finally, numerous operating heads 2 may be used with the handle 4.

FIGS. 4 THROUGH 7

FIGS. 4 through 7 illustrate various alternative arrangements for driving rotatable cable 26 which will be described hereinafter. Components of these embodiments which are identical to those of the fluid powered brush system A illustrated in FIGS. 1 to 3 will be given like reference numerals.

Referring to FIG. 4, the impeller housing E is disposed such that it extends substantially parallel to supply pipe F. Specifically, impeller housing E is detachably connected to conduit 51 which extends substantially perpendicular to pipe F. In this embodiment, a wall 52 directs all of the fluid flowing through pipe F into the impeller housing E to rotate impeller 34. The fluid is subsequently directed out of the impeller housing E and through shower head D.

In the embodiment depicted in FIG. 5, an impeller 54 is disposed in the shower head D. The impeller 54 has a plurality of vanes 56 extending outwardly therefrom and is secured to bevel gear 58. Shaft 60 rotatably supports the bevel gear 58 and impeller 54 in the shower head D. A bevel gear 62 is positioned in meshing engagement with bevel gears 58 and 64. The cable 26 (not shown) is nonrotatably secured to bevel gear 64. Three supply conduits 40 direct fluid to the impeller 54 to rotate the same.

As best seen in FIGS. 6 and 7, the toothbrush B may be drivingly connected to an external body brush I. The external body brush I includes a plurality of brush heads 66 which are preferably driven in a similar manner to brushes 6 illustrated in FIGS. 1 through 3. The flexible cord C includes a detachable support sleeve 68 for detachably securing the same to external body brush I. The support collar 68 includes a flexible annular collar 70. The collar 70 mates with flexible annular collar 72 of shoulder 74. Flexible cable 26 includes a pin 75 inserted in a corresponding hole in shaft 76. A bevel gear 78 is formed on the innermost end of shaft 76. Gear 78 is disposed in meshing engagement with the bevel gear 80 extending from the immediately adjacent brush head 66. Although not shown, a similar arrangement may be used to detachably secure the cord C to the impeller housing E and/or shower head D.

FIGS. 8 THROUGH 11

The above-identified figures depict alternative arrangements for toothbrush B which will hereinafter be described.

Referring to FIG. 8, toothbrush J includes an operating head 82 and a handle 84. A shaft 86 extends through operating head 82 and handle 84 and is rotatably supported therein by shoulders 88. A pair of brushes 90 extend from the lower surface of operating head 82 and are identical in configuration to brushes 6 illustrated in FIG. 3. Bevel gears 92 extend around the upper surface of each of the brushes 90. A pair of bevel gears 94 are fixed to output shaft 86 and disposed in meshing engagement with corresponding bevel gears 92. Four impellers 96 are spaced along output shaft 86 in handle 84. Referring to FIG. 9, the impellers 96 include a plurality of vanes 98 extending outwardly therefrom. As seen in FIG. 10, impellers 96 may be provided with arcuately shaped vanes 100.

A plate 102 separates handle 84 into a working chamber 104 and a reservoir chamber 106. The plate 102 has a plurality of apertures 108 formed therein. A supply line 110 includes a first end which is disposed in handle 84. The other end of supply line 110 is preferably connected upstream of the shower head such that a portion of the water flowing to the shower head is drawn off and directed to toothbrush J. The supply line 110 includes four outlet ports 112 disposed directly above corresponding impellers 96. A control valve 114 is positioned upstream of the outlet ports 112 to prevent the flow of fluid therethrough. Upon depression of the control valve 114, fluid is permitted to flow through the outlet ports 112 to turn impellers 96 which subsequently rotate brushes 90.

A drain 116 is formed in the handle 84 to drain fluid from reservoir chamber 106. A drain tube may be connected to drain 116 to direct fluid away from the individual and to the shower drain. A conduit 118 extends between the reservoir chamber 106 and opening 120 formed in operating head 82. A control valve 122 similar to control valve 114 regulates the flow of fluid through conduit 118. Upon depression of the control valve 122, fluid from the reservoir chamber 106 is permitted to flow through the conduit 118 and out opening 120 to provide the user with fluid to rinse his or her mouth.

This embodiment is a significant improvement over previously known fluid powered brushes. More specifically, the brush J avoids substantial discrepancies in the drive force imparted on each of the brush heads 90. Thus, the brush heads may be rotated at substantially the same speed. Further, this arrangement readily enables an individual to rinse his or her mouth.

Referring to FIG. 11, toothbrush K includes an operating head 124 and a handle 126. The operating head 124 is identical to operating head 82 of toothbrush J. Also, conduit 128 and control valve 130 are identical to conduit 118 and valve 122 of toothbrush J. Plate 132 rotatably supports four impellers 134. The vanes of impellers 134 can be configured in either the manner shown in FIG. 9 or FIG. 10. A bevel gear 136 is fixed to each of the impellers 134 via shaft 138. Four bevel gears 140 are fixed to output shaft 142 and are disposed in meshing engagement with corresponding bevel gears 136. Thus, shaft 142 rotates upon rotation of impellers 134.

Supply conduit 144 extends in handle 126 and includes four outlet ports 146 disposed directly adjacent corresponding impellers 134. Although not shown, a control valve similar to control valve 114 of toothbrush J may be provided to control the flow of fluid through supply conduit 144. The opposite end of supply conduit 144 is connected upstream of the shower head E, as shown in FIG. 12. A wall 148 directs all of the fluid passing through pipe F to supply line 144.

Plate 150 separates handle 126 into a working chamber 152 and a reservoir chamber 154. A plurality of apertures 156 are formed in plate 150 to permit fluid to flow therethrough. A one way valve 158 is associated with each of the apertures 156. The one way valves 158 prevent fluid in the reservoir 154 from flowing into working chamber 152. A return conduit 160 communicates with reservoir chamber 154 and directs the fluid back to pipe F so that it may emitted through shower head E.

This embodiment includes all of the advantages discussed in connection with toothbrush J. In addition, the toothbrush K minimizes the fluid drawn off from the shower by redirecting most if not all of the fluid to the shower head via return conduit 160.

While this invention has been described as having a preferred design, it is understood that it is capable of further modifications, uses and/or adaptions of the invention following in general the principle of the invention including such departures from the present disclosure as come within the known or customary practice in the art to which the invention pertains, and as may be applied to the essential features set forth, and fall within the appended claims.

I claim:

1. A fluid powered brush system, comprising:
   a) a body member having at least one brush element rotatably mounted thereon;
   b) a shower head having an outlet for dispensing fluid therethrough;
   c) a fluid supply pipe having an inlet and being connected to said shower head such that fluid passing through said fluid supply pipe is emptied through said outlet of said shower head;
   d) an impeller adapted to be driven by a fluid for driving said brush element, said impeller being positioned intermediate said outlet of said shower head and said inlet of said fluid supply pipe and adapted to receive fluid flowing through said fluid supply pipe; said impeller having an axis which is substantially parallel to the direction of extension of the portion of said supply pipe directly adjacent the impeller; and
   e) a flexible drive member having first and second ends, said first end having a first means drivingly connected to said impeller and said second end having a second means drivingly connected to said brush element.

2. A system as in claim 1, further including:
   a) said first means comprising first and second gears, said first gear having a diameter greater than said second gear, said first gear being operably connected to said impeller and in meshing engagement with said second gear, said second gear being operably connected to said second end of said flexible drive member.

3. A system as in claim 2, further including:
   a) an impeller housing for housing said impeller, said impeller housing being positioned upstream of said shower head.

4. A system as in claim 3, wherein:
   a) said first and second gears are positioned in said impeller housing.

5. A system as in claim 1, wherein:
   a) said impeller is positioned in said shower head.

6. A system as in claim 1, wherein:
   a) said body member includes a handle and an operating head, said at least one brush element is rotatably mounted on said operating head.

7. A system as in claim 6, wherein:
   a) said operating head is detachably connected to said handle.

8. A system as in claim 1, wherein:
   a) said body member includes a hollow cavity; and,
   b) said first end of said flexible drive member is positioned in said hollow cavity.

9. A system as in claim 8, wherein:
   a) said brush element includes upper and lower surfaces, said upper surface is positioned in said hollow cavity; and,
   b) a plurality of bristles extend from said lower surface.

10. A system as in claim 9, wherein said second means comprises:
    a) a first gear is connected to said upper surface of said brush element; and
    b) a second gear is connected to said flexible drive member and in meshing engagement with said first gear.

11. A fluid powered brush system, comprising:
    a) a body member having at least one brush element rotatably mounted thereon;
    b) fluid dispensing means having an outlet for dispensing a fluid through said outlet, said fluid dispensing means being one of a shower head and a faucet;
    c) a fluid supply pipe being connected to said fluid dispensing means;
    d) an impeller adapted to be driven by a fluid for driving said brush element, said impeller being positioned upstream of said outlet and adapted to receive fluid flowing through said supply pipe;
    e) a flexible drive member having first and second ends, said first end being drivingly connected to said brush element, said second end being positioned adjacent said impeller; and,
    f) first and second gears, said first gear having a diameter greater than said second gear, said first gear being operably connected to said impeller and in meshing engagement with said second gear, said second gear being operably connected to said second end of said flexible tube.

12. A system as in claim 11, wherein:
    a) said fluid supply pipe is connected to said fluid dispensing means such that all fluid passing through said fluid supply pipe is emptied through said outlet of said fluid dispensing means.

13. A system as in claim 11, wherein:
    a) said fluid dispensing means is a shower head.

14. A system as in claim 13, wherein:
    a) said impeller is positioned is said shower head.

15. A system as in claim 11, further including:
    a) an impeller housing for housing said impeller, said impeller housing being positioned upstream of said fluid dispensing means.

16. A system as in claim 15, wherein:
    a) said first and second gears are positioned in said impeller housing.

17. A system as in claim 16, wherein:
    a) said operating head is detachably connected to said handle.

18. A system as in claim 11, wherein:
    a) said body member includes a handle and an operating head, said at least one brush element is rotatably mounted on said operating head.

19. A system as in claim 11, wherein:
    a) said body member includes a hollow cavity; and,
    b) said first end of said flexible drive member is positioned is said hollow cavity.

20. A system as in claim 11, wherein:
    a) said first and second gears are positioned in said fluid dispensing means.

* * * * *